US00PP15554P3

(12) United States Plant Patent
Goemans

(10) Patent No.: US PP15,554 P3
(45) Date of Patent: Feb. 15, 2005

(54) ***ALSTROEMERIA* PLANT NAMED 'ROSELIND'**

(50) Latin Name: *Alstroemeria hybrid*
Varietal Denomination: Roselind

(75) Inventor: Robert Adrian Goemans, Chichester (GB)

(73) Assignee: Wulfinghoff Alstroemeria B.V.

( * ) Notice: Subject to any disclaimer, the term of this patent is extended or adjusted under 35 U.S.C. 154(b) by 4 days.

(21) Appl. No.: 10/097,255

(22) Filed: Mar. 15, 2002

(65) Prior Publication Data

US 2003/0177560 P1 Sep. 18, 2003

(51) Int. Cl.[7] ..... A01H 5/00

(52) U.S. Cl. ..... Plt./309

(58) Field of Search ..... Plt./309

*Primary Examiner*—Kent Bell
*Assistant Examiner*—Louanne Krawczewicz Myers

(57) ABSTRACT

A new and distinct *Alstroemeria* plant named 'Roselind' characterized as suitable for pots larger than 7 cm; growth height 10–30 cm under greenhouse conditions; bushy-dwarf growth habit; red flowers with yellow from base to mid section with stripes on at least 2 of the 3 inner tepals (upper surface); and 3 weeks inflorescence longevity on the plant; 12 days as a cut flower.

1 Drawing Sheet

Latin name of the genus and species of the claimed plant: *Alstroemeria hybrid.*
Variety denomination: 'Roselind'.

BACKGROUND OF THE NEW VARIETY

The present invention comprises a new and distinct cultivar of *Alstroemeria* plant, hereinafter referred to by the cultivar name 'Roselind'.

'Roselind' originated from a hybridization made in a controlled breeding program in Chichester in Sussex, United Kingdom by the inventor Robert Adrian Goemans. The female parent is an unnamed, unpatented *Alstroemeria aurea* selection. The male parent of 'Roselind' is an unnamed dwarf 'Butterfly' type cultivar (unpatented).

'Roselind' was discovered and selected as one flowering plant within the progeny of the stated parentage by Robert Adrian Goemans in 1998 in a controlled environment in Chichester, United Kingdom. The first act of asexual reproduction of 'Roselind' was accomplished when vegetative cuttings were taken from the initial selection in May, 1999 in a controlled environment in Chichester, United Kingdom. Horticultural examination of selected plants initiated in 1999 has demonstrated that the combination of characteristics as herein disclosed for 'Roselind' are firmly fixed and retained through successive generations of asexual reproduction.

BRIEF SUMMARY OF THE INVENTION

The following traits have been repeatedly observed and are determined to be basic characteristics of which in combination distinguish this *Alstroemeria* as a new and distinct cultivar:

1. Suitable for pots larger than 7 cm;
2. Growth height 10–30 cm under greenhouse conditions;
3. Bushy-dwarf growth habit;
4. Red flowers with yellow from base to mid section with stripes RHS 187A on at least 2 of the 3 tetals (inner tepals, upper surface); and 5. 3 weeks inflorescence longevity on the plant; 12 days as a cut flower.

There are no commercial cultivars known to the inventor, similar in comparison to 'Roselind'. In comparison to 'Roselind', the female parental cultivar has orange flowers and is tall in size; and the male parental cultivar has blue flowers and is small in size, having a dwarf growth habit.

'Roselind' has not been observed under all possible environmental conditions. The phenotype may vary significantly with variations in environment such as temperature, light intensity and day length, without any change in genotype. The following observations, measurements and comparisons describe plants grown in Chichester, Sussex, United Kingdom under greenhouse conditions which approximate those generally used in commercial practice.

BRIEF DESCRIPTION OF THE DRAWINGS

The accompanying photograph shows a typical plant of the new variety with colors as accurate as possible.

The photographic drawing shows the flowers and foliage of 'Roselind'.

DETAILED BOTANICAL DESCRIPTION

In the following description, color references are made to The Royal Horticultural Society Colour Chart (R.H.S.). The color values were determined in the afternoon of Sep. 28, 2001 under normal daylight conditions in Wateringen, The Netherlands. The plants described are nine months of age and grown in 15 cm pots.

Classification:
*Botanical.*—*Alstroemeria* hybrid.
*Commercial.*—*Alstroemeria* cv. 'Roselind'.
Plant:
*Form.*—Pot Plant.
*Height.*—10–30 cm (Dutch greenhouse conditions).

*Diameter.*—30 cm (at 6 months of age).

*Growth.*—Bushy-dwarf growth habit.

*Time it takes to produce a flowering plant.*—From planting of rooted tissue cultured rhizomes to flowering is 6 to 9 months, depending on cultural conditions.

*Number of lateral branches.*—36.

*Size.*—10 cm in length, 5 mm in diameter.

*Length of internode.*—6 mm. Internode Color: RHS yellow-green group 145B.

Foliage:

*Quantity.*—5–10 leaves on each centimeter of stem, depending on growth stage.

*Size of leaf.*—Length: 35–75 mm; width: 10–20 mm.

*Shape of leaf.*—Oblong-ovate; subacute apex; cuneate base; entire margin.

*Texture.*—Smooth and firm.

*Color.*—Upper side is dark green, RHS 137 B. Underside is light-green, RHS 138 C.

Rhizomes:

*Color.*—White, RHS 158 A to RHS 158 D.

*Size.*—Length 10–50 mm; diameter 6–15 mm, depending on age.

Inflorescence:

*Number of flowers per cyme.*—1–2.

*Number of cymes per umbel.*—2–3.

*Number of flowers per lateral stem.*—2–4.

*Number of flowers per plant.*—12–15.

*Flowering season.*—May–September under outdoor conditions.

*Fragrance.*—None.

*Bud.*—Form: Tubular pointed. Diameter: 10–20 mm. Length: 15–25 mm.

*Peduncle.*—20–25 mm, medium-green, RHS 145 A to RHS 145 D.

*Color.*—Red RHS 54A to RHS 145 A to RHS 145 D.

*Flower.*—Size: Medium, length: 40–60 mm; width: 40–60 mm. Shape: Broad obovate.

*Tepals.*—Shape: Broad obovate. Arrangement: 2 whorls of 3 tepals, with each flower consisting of 6 tepals total. Size: Length: 55 mm, width: 30 mm. Apex: Emarginate. Base: Cuneate. Margin: Serrate. Texture: Silky.

*Color.*—Upper surface of 3 outer tepals: Red, RHS 54 A to RHS 54 D. Under surface of 3 outer tepals: Red, RHS 54A to RHS 54 D. Upper surface of 3 inner tepals: RHS red-purple 66 D, yellow from base to mid section, RHS 13A to RHS 13B, on at least 2 of the 3 tepals. Lower surface of 3 inner tepals: RHS red-purple 66D, yellow from base to mid section, RHS 9B, on at least 2 of the 3 tepals. Markings: RHS 187A on at least 2 of the 3 inner tepals (upper surface).

*Peduncle.*—Length: 40–50 mm. Color: Medium-green, RHS 145 A to RHS 145 D.

*Lasting quality.*—Approximately 3 weeks on the plant; 12 days as a cut flower.

Reproductive organs:

*Stamens.*—6.

*Pollen.*—Plentiful, yellow RHS 9 B.

*Anthers.*—Yellow, RHS 13 A.

*Filaments.*—Red, RHS 63 A to RHS 63 D.

*Pistils.*—1, Color red-pink, RHS 63 A to RHS 63 D.

*Stigma.*—Pink-white, RHS 36 A to RHS 36 C.

*Seeds.*—None.

Disease/pest resistance/susceptibility: No known information.

I claim:

1. I claim a new and distinct cultivar of *Alstroemeria* plant named 'Roselind', as described and illustrated herein.

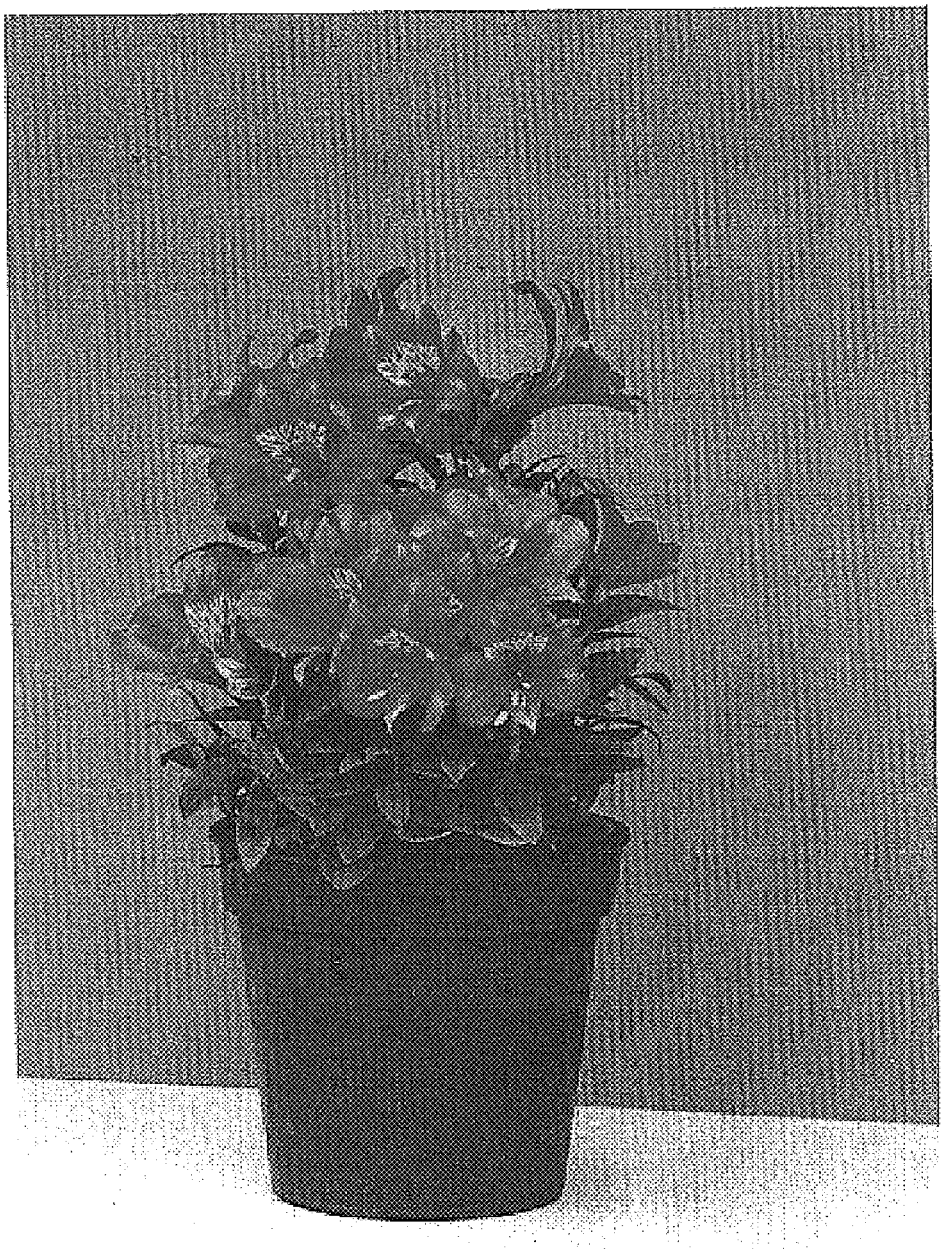

* * * * *